United States Patent
O'Farrell et al.

(10) Patent No.: US 9,547,015 B2
(45) Date of Patent: Jan. 17, 2017

(54) KITS AND METHODS FOR CYANIDE DETECTION

(71) Applicant: Diagnostic Consulting Network, Inc., Carlsbad, CA (US)

(72) Inventors: Brendan O'Farrell, Carlsbad, CA (US); Hans Boehringer, San Diego, CA (US); Roy Chung, Carlsbad, CA (US); Winnie Tong, Carlsbad, CA (US)

(73) Assignee: DIAGNOSTIC CONSULTING NETWORK, INC., Carlsbad, CA (US)

( * ) Notice: Subject to any disclaimer, the term of this patent is extended or adjusted under 35 U.S.C. 154(b) by 0 days.

(21) Appl. No.: 14/793,538

(22) Filed: Jul. 7, 2015

(65) Prior Publication Data
US 2015/0309056 A1 Oct. 29, 2015

Related U.S. Application Data

(62) Division of application No. 13/830,302, filed on Mar. 14, 2013, now Pat. No. 9,110,029.

(60) Provisional application No. 61/690,378, filed on Jun. 25, 2012.

(51) Int. Cl.
| | |
|---|---|
| G01N 33/84 | (2006.01) |
| G01N 21/78 | (2006.01) |
| G01N 33/53 | (2006.01) |
| G01N 33/50 | (2006.01) |

(52) U.S. Cl.
CPC .............. *G01N 33/84* (2013.01); *G01N 21/78* (2013.01); *G01N 33/5308* (2013.01); *G01N 33/5014* (2013.01)

(58) Field of Classification Search
None
See application file for complete search history.

(56) References Cited

U.S. PATENT DOCUMENTS

| | | | |
|---|---|---|---|
| 6,627,460 B1 | 9/2003 | Lihme et al. | |
| 2005/0037514 A1* | 2/2005 | Carron | G01N 21/658 436/171 |
| 2008/0096281 A1 | 4/2008 | Geddes et al. | |
| 2008/0227746 A1 | 9/2008 | Boss et al. | |
| 2010/0273677 A1 | 10/2010 | Lund-Johansen | |

(Continued)

FOREIGN PATENT DOCUMENTS

| | | |
|---|---|---|
| EP | 1 016 865 | 7/2000 |
| WO | WO-2011/116006 | 9/2011 |

OTHER PUBLICATIONS

Ma et al., Rapid Point of Care Analyzer for the Measurement of Cyanide in Blood, Analytical Chemistry, 2011, 83, pp. 4319-4324.*

(Continued)

*Primary Examiner* — Rebecca Martinez
(74) *Attorney, Agent, or Firm* — Morrison & Foerster LLP

(57) ABSTRACT

Provided herein are compositions, kits, methods and devices for cyanide detection, particularly for cyanide detection in biological samples such as whole blood. The method comprises (1) contacting a sample with a cobinamide conjugate comprising a cobinamide moiety and a carrier; and (2) measuring the absorbance of light by the cobinamide conjugate. The present disclosure provides field-deployable cyanide detection methods, compositions, kits and devices, which provide rapid, accurate readout at the point of contact. Further provided herein is a method for determining exposure of a subject to cyanide.

20 Claims, 10 Drawing Sheets

(56) References Cited

U.S. PATENT DOCUMENTS

| | | |
|---|---|---|
| 2010/0330684 A1 | 12/2010 | O'Connor |
| 2013/0005044 A1* | 1/2013 | Boss .................... G01N 31/22 436/109 |

OTHER PUBLICATIONS

Baskin et al., in "Medical Aspects of Chemical and Biological Warfare," Sidell, et al. (eds.) TMM publications, Washington, (1997) pp. 271-286.

Baud et al., "Elevated blood cyanide concentrations in victims of smoke inhalation," N Engl J Med. (1991) 325(25):1761-1766.

Boehringer et al., "A field-deployable device for the rapid detection of cyanide poisoning in whole blood," Proc. SPIE (2012) 8371: 83710Z-1-83710Z-10.

Brenner et al., "Comparison of cobinamide to hydroxocobalamin in reversing cyanide physiologic effects in rabbits using diffuse optical spectroscopy monitoring," J Biomed Opt (2010) 15(1):017001-1-017001-8.

Broderick et al., "Nitric oxide scavenging by the cobalamin precursor cobinamide," J Biol Chem. (2005) 280(10):8678-8685.

Clark et al., "Blood carboxyhaemoglobin and cyanide levels in fire survivors," Lancet (1981) 1(8234):1332-1335.

Coyne et al., "Synthesis of a covalent gemcitabine-(carbamate)-[anti-HER2/neu] immunochemotherapeutic and its cytotoxic antineoplastic activity against chemotherapeutic-resistant SKBr-3 mammary carcinoma," Bioorg Med Chem (2011) 19(1):67-76.

Fox et al., "Detection of Aspergillus fumigatus mycotoxins: immunogen synthesis and immunoassay development," J Microbiol Methods (2004) 56(2):221-230.

International Search Report and Written Opinion for PCT/US2013/047181, issued Mar. 31, 2014, 11 pages.

International Preliminary Report on Patentability for PCT/US2013/047181, mailed Dec. 31, 2014, 7 pages.

Ishii et al., "Determination of cyanide in whole blood by capillary gas chromatography with cryogenic oven trapping," Anal Chem. (1998) 70(22):4873-4876.

Ma et al., "Rapid point of care analyzer for the measurement of cyanide in blood," Anal Chem (2011) 83(11):4319-4324.

Mai et al., "Application of polymer conjugate using polylysine as a carrier in detection of hepatitis C virus core antigen," Chin J Biologicals (2010) 23(11):1239-1243.

Moriya et al. "Potential for error when assessing blood cyanide concentrations in fire victims," J Forensic Sci. (2001) 46(6):1421-1425.

Pettigrew et al., "Microdiffusion method for estimation of cyanide in whole blood and its application to the study of conversion of cyanide to thiocyanate," Clinical Chemistry (1973) 19(5):466-471.

Renz, "Some Intermediates in the Biosynthesis of Vitamin B12," Methods Enzymol. (1971) 18:82-92.

Vo et al., Development of a Cobineamide-Based Cyanide Sensor for Rapid Detection of Cyanide Toxicity, American Society International Conference Abstracts, Conference May 13-18, 2011, Abstract: A5861.

Way, "Cyanide intoxication and its mechanism of antagonism," Ann Rev Pharmacol Toxicol (1984) 24:451-481.

Restriction Requirement for U.S. Appl. No. 13/830,302, issued Dec. 13, 2013, 9 pages.

Response to Restriction Reqirement for U.S. Appl. No. 13/830,302, filed Jan. 13, 2014, 5 pages.

Office Action for U.S. Appl. No. 13/830,302, issued Mar. 27, 2014, 11 pages.

Response to Office Action for U.S. Appl. No. 13/830,302, filed Jun. 27, 2014, 45 pages.

Final Office Action for U.S. Appl. No. 13/830,302, issued Oct. 21, 2014, 12 pages.

Communication pursuant to Rules 161(1) and 162 EPC for EP 13826668.9, issued Feb. 5, 2015, 2 pages.

Response to Final Office Action for U.S. Appl. No. 13/830,302, filed Mar. 20, 2015, 13 pages.

Notice of Allowance for U.S. Appl. No. 13/830,302, issued Apr. 10, 2015, 8 pages.

Response to Communication pursuant to Rules 161(1) and 162 EPC for EP 13826668.9, filed Aug. 12, 2015, 17 pages.

Communication pursuant to Article 94(3) EPC for EP 13826668.9, issued Dec. 14, 2015, 6 pages.

Response to Communication pursuant to Article 94(3) EPC for EP 13826668.9, filed Jun. 24, 2016, 14 pages.

* cited by examiner

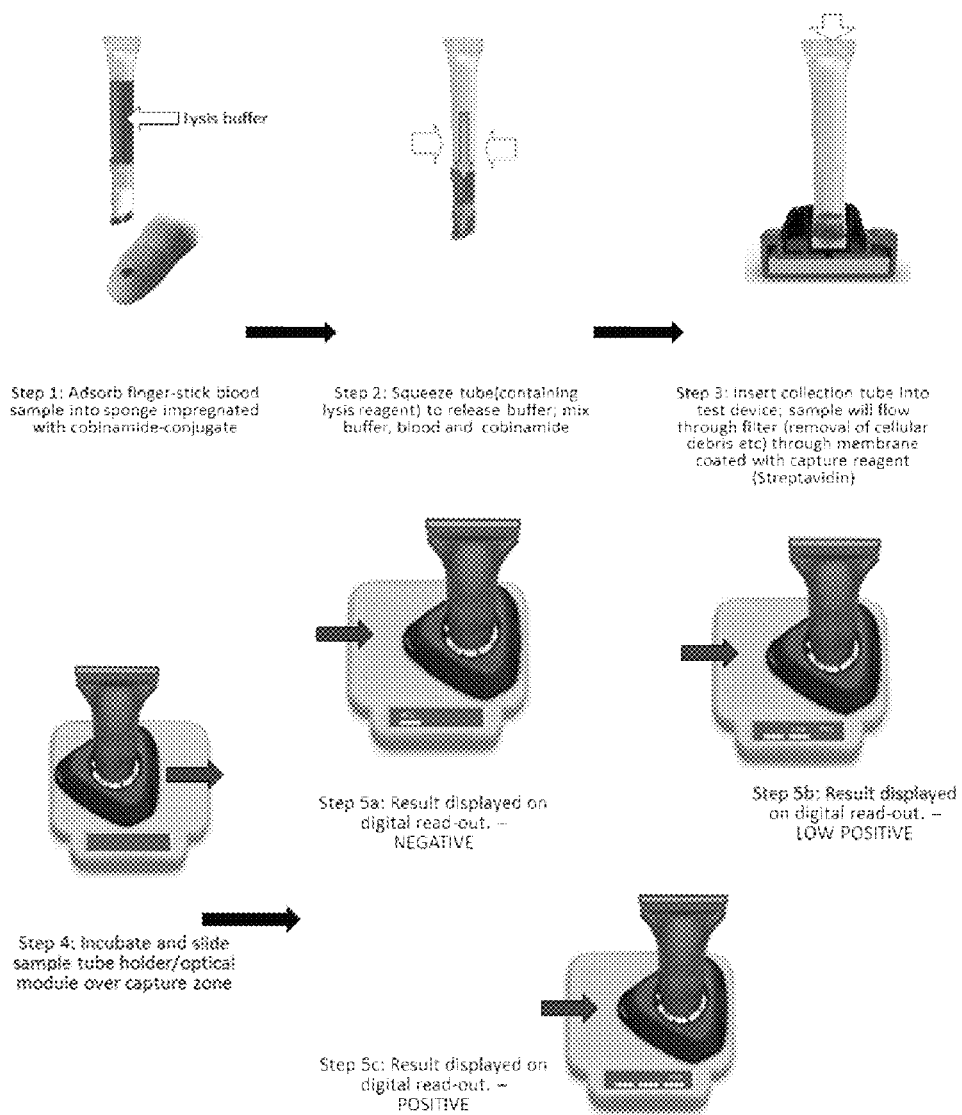

KITS AND METHODS FOR CYANIDE DETECTION

CROSS REFERENCE TO RELATED APPLICATIONS

This application is a divisional application of U.S. patent application Ser. No. 13/830,302, filed Mar. 14, 2013, now pending, which claims the benefit of U.S. Provisional Patent Application Ser. No. 61/690,378, filed Jun. 25, 2012. The contents of the applications listed above are incorporated herein by reference in their entireties for all purposes.

STATEMENT REGARDING FEDERALLY SPONSORED RESEARCH OR DEVELOPMENT

This invention was made with the CounterACT Program, Office of the Director, National Institutes of Health (OD) and the National Institute of Neurological Disorders and Stroke (NINDS), Grant Number 1R43NS076359-01. The U.S. government may have certain rights in this invention.

TECHNICAL FIELD

The present invention is in the field of cyanide detection, and relates to the areas of field-deployable cyanide detection methods, compositions, kits and devices. Specifically, the present invention relates to cyanide detection in biological samples.

BACKGROUND

Hydrogen cyanide gas is an important toxin in smoke from industrial and residential fires, industrial accidents and release through acts of terrorism. Cyanide acts extremely rapidly and can cause death within minutes. In the United States, there are approximately 5,000-10,000 deaths due to smoke inhalation annually. Cyanide may be responsible for many of these deaths, because it is released from the combustion of plastics, wool, and other nitrogen-containing materials.

Combustion of synthetic products that contain carbon and nitrogen, such as plastics and synthetic fibers, releases cyanide. There have been numerous studies of fire victims to assess the lethal levels of cyanide. Fire survivors have been found to have <20 µM cyanide in blood, while victims were found to have levels greater than 20-30 µM and in some cases as much as 100 µM cyanide in blood (Baud et al., 1991, N. Engl. J. Med., 325: 1761-1766). Cigarette smoke also contains cyanide. The nonsmoker typically averages about 0.06 µg/mL (2.31 µM) of cyanide in blood, whereas a smoker typically averages 0.17 µg/mL (6.5 µM) (Clark et al., 1981, Lancet: 1332-1335).

Cyanide is also readily used in industry in the making of plastics, in the recovery of gold and silver from ores, and in the electroplating of metals, such as silver, gold, platinum and copper (Baskin and Brewer, In Medical Aspects of Chemical and Biological Warfare, Eds. Sidell, Takafuji and Franz, TMM publications, Washington, 1997, Chapter 10, pages 271-286). Cassava root, which is used to make tapioca and is a major food source in tropical regions, releases cyanide when improperly prepared, and chronic cyanide exposure leads to konzo or tropical ataxic neuropathy. The drug sodium nitroprusside, a nitric oxide releasing agent used to treat patients with acute hypertension, releases five cyanide ions for every nitric oxide molecule and is limited by cyanide toxicity. Due to its toxicity when inhaled or ingested, cyanide could also be used as a terrorist weapon.

Therefore, there exists a need to frequently and efficiently monitor cyanide amount in the environment and in the human body to evaluate cyanide exposure and its associated risks. In cases of cyanide poisoning or suspected cyanide poisoning, there exists a need to rapidly measure cyanide amount for treatment decisions.

A variety of methods exist for measuring cyanide levels. These include a variety of chemical approaches and expensive techniques, including spectrophotometry, fluorometry, high performance liquid chromatography (HPLC), mass spectrometry, HPLC-mass spectrometry, and gas chromatography. Spectrophotometric assays can analyze multiple samples relatively quickly, but lack sensitivity and specificity, while gas chromatography, mass spectrometry, and HPLC require expensive equipment and allow only limited sample throughput. Several existing methods require laborious multistep sample pre-treatment are not amenable for use in the field. Neither does there exist an integrated device which processes the sample, induces and controls the chemical reactions and provides an objective measure of cyanide within the sample. Thus, a field-deployable device for rapid cyanide detection is clearly needed.

SUMMARY OF THE INVENTION

Assays, methods, kits and devices for detecting cyanide are disclosed. In one aspect, a method for detecting cyanide in a sample is provided. In one embodiment, the method comprises contacting a sample with a cobinamide conjugate comprising a cobinamide moiety and a carrier, and measuring the absorbance of light by the cobinamide conjugate.

In certain embodiments, the cobinamide moiety is dihydroxycobinamide. Without being bound by any theory, monocyanocobinamide or other cobinamide derivatives may be used.

In certain embodiments, the carrier is a molecule, such as a polypeptide. In certain embodiments, the carrier molecule is biotinylated or can be otherwise modified for use in the present invention. In one aspect, the polypeptide is a polypeptide, such as a polylysine, a polytyrosine, and a polythreonine, or an immunoglobulin.

In other embodiments, the carrier is a surface. The surface can be a plastic surface, or a surface comprised in a nitrocellulose membrane, a nylon membrane, a latex particle, or a gold particle.

In one aspect, the cobinamide conjugate comprises a multiplicity of cobinamide moieties. In one embodiment, the cobinamide moiety is conjugated to the carrier via a non-covalent interaction. In another embodiment, the cobinamide moiety is conjugated to the carrier covalently. In an alternative embodiment, the instant invention provides a method for detecting cyanide in accordance with any combination of the preceding embodiments.

In another aspect, the cobinamide moiety is conjugated to the carrier by a covalent bond involving the OH group of the cobinamide moiety. In one embodiment, the covalent bond is between the OH group of the cobinamide moiety and a nucleophilic group. In one embodiment, the nucleophilic group is the $NH_2$ group of a polylysine. In certain aspects, the OH group of the cobinamide moiety is activated by carbodiimadizole, or another suitable diimidazole, or another suitable crosslinker to form the covalent bond. In a preferred embodiment, cobinamide forms a covalent bond between the OH group of cobinamide and an $NH_2$ group of polylysine (a nucleophilic group). The terminal OH group of cobinamide is activated by carbodiimadizole which then reacts with an NH$_2$ group of the polylysine. The structure of the cobinamide is such that the NH$_2$ groups of the cobinamide are not reactive to the activated OH group. In other embodiments, polytyrosine or polythreonine is used instead of polylysine.

In yet another aspect, the covalent bond is between the OH group of the cobinamide moiety and an isocyanate moiety. The isocyanate moiety can be comprised in N-[p-maleimidophenyl]isocyanate (PMPI). In one aspect, the maleimide moiety of PMPI forms a covalent bond with a sulfhydryl group. In certain embodiments, the sulfhydryl group can be comprised in the carrier. In another aspect, the isocyanate moiety is comprised in a molecule comprising a multiplicity of NH$_2$ groups each capable of reacting with an activated ester. In certain aspects, a multiplicity of the activated esters are comprised in a molecule, a particle, or a surface. In certain embodiments, a multiplicity of cobinamide moieties are conjugated to the multiplicity of activated esters comprised in the molecule, particle, or surface. In an alternative embodiment, the instant invention provides a method for detecting cyanide in accordance with any combination of the preceding embodiments.

In certain embodiments, the method disclosed herein detects the presence or absence of cyanide in a sample. In one aspect, the method detects the amount of cyanide in the sample quantitatively. In one other aspect, the method detects cyanide in the sample qualitatively.

In some embodiments, the method disclosed herein further comprises comparing the absorbance of light by the cobinamide conjugate with a control feature. In certain embodiments, the absorbance of light is measured and compared with a reference or background. In certain aspects, the reference or background is measured at a wave length greater than 650 nm. In other aspects, the reference or background is measured at a wave length of about 650 nm.

In one aspect, the absorbance of light in the method disclosed herein is measured at a visible wavelength. In certain embodiments, the absorbance of light is measured at a wavelength of about 400 nm to about 700 nm. In certain aspects, the absorbance of light is measured at a wavelength of about 400 nm to about 500 nm, about 500 nm to about 600 nm, or about 600 nm to about 700 nm. In one aspect, the wavelength used is of about 500 nm to about 520 nm, preferably of about 500 nm to about 510 nm, and more preferably of about 505 nm. In another aspect, the wavelength used is of about 520 nm to about 540 nm, preferably of about 525 nm to about 535 nm, and more preferably of about 531 nm. In certain aspects, the wavelength used is of about 540 nm to about 560 nm, or of about 560 nm to about 580 nm. In another aspect, the wavelength used is of about 580 nm to about 600 nm, preferably of about 580 nm to about 590 nm, and more preferably of about 583 nm.

In another aspect, the absorbance of light in the method disclosed herein is measured at an invisible wavelength. In certain embodiments, the absorbance of light is measured at a wavelength of about 250 nm to about 400 nm. In certain aspects, the absorbance of light is measured at a wavelength of about 250 nm to about 300 nm, about 300 nm to about 350 nm, or about 350 nm to about 400 nm. In one aspect, the wavelength used is of about 350 nm to about 400 nm, preferably of about 360 nm to about 380 nm, more preferably of about 360 nm to about 370 nm, and even more preferably of about 366 nm.

In certain embodiments, the method disclosed herein detects the presence or absence of cyanide in a sample, and the sample is contacted with the cobinamide conjugate without any pre-treatment. In certain other embodiments, the sample is pre-treated. In one aspect, the sample can be a biological sample, such as blood. In one embodiment, the blood sample is treated to remove red blood cells. Without being bound by any theory, the treatment to remove red blood cells can be performed before, after, or at about the same time when the sample is contacted the cobinamide conjugate.

In one aspect, the method disclosed herein is completed in about five minutes. In one aspect, the method disclosed herein is completed in less than five minutes.

In one aspect, the amount of cyanide in the sample to be detected by the method disclosed herein is from about 7.5 µM to about 1000 µM. In preferred embodiments, the method disclosed herein detects in a sample biologically or physiologically relevant amounts of cyanide.

In some embodiments, the instant invention provides a method for detecting cyanide in accordance with any combination of the preceding embodiments.

In another aspect, provided herein is a kit for detecting cyanide in a sample, comprising a cobinamide conjugate, said cobinamide conjugate comprising a cobinamide moiety and a carrier. In one embodiment, the kit further comprises a composition for sample collection. In another embodiment, the kit further comprises a composition for sample processing. In yet another embodiment, the kit further comprises a composition for capturing the cobinamide conjugate.

In certain embodiments, the carrier is a molecule, such as a polypeptide. In certain embodiments, the carrier molecule is biotinylated or can be otherwise modified for use in the present invention. In one aspect, the polypeptide is a polylysine or an immunoglobulin.

In other embodiments, the composition for capturing the cobinamide conjugate is comprised in a surface. The surface can be a plastic surface, or a surface comprised in a nitrocellulose membrane, a nylon membrane, a latex particle, or a gold particle. In one embodiment, the composition for capturing the cobinamide conjugate of the invention is capable of capturing a multiplicity of the cobinamide conjugates.

In some embodiments, the instant invention provides a kit for detecting cyanide in accordance with any combination of the preceding embodiments.

In yet another aspect, provided herein is a device for detecting cyanide in a sample, comprising a chamber for housing a cobinamide conjugate, said cobinamide conjugate comprising a cobinamide moiety and a carrier. In one embodiment, the device further comprises a detector, wherein the detector detects the absorbance of light by the cobinamide conjugate. In some embodiments, the device further comprises a display indicating the presence or absence of cyanide in the sample, or the amount of cyanide in the sample.

In some embodiments, the device further comprises a second chamber for sample collection, wherein the second and first chambers can be the same or different. The chamber for sample collection can comprise a material impregnated with the cobinamide conjugate. In some embodiments, the material impregnated with the cobinamide conjugate can be a sponge, a paper, and a porous membrane. Other materials suitable for the purpose of the present invention can also be used.

In some embodiments, the device further comprises a third chamber for housing a composition for sample processing. In one aspect, the device further comprises a means for separating the cobinamide conjugate from the sample. In one embodiment, the device further comprises a means for capturing the cobinamide conjugate. In one aspect, the means for capturing the cobinamide conjugate can be a surface adapted to allow measurement of the absorbance of light by the captured cobinamide conjugate. Such a surface can be comprised in a membrane or particle, for example, a nitrocellulose membrane, a nylon membrane, a latex particle, or a gold particle.

In some embodiments, the instant invention provides a device for detecting cyanide in accordance with any combination of the preceding embodiments.

In yet another aspect, provided herein is a method for determining exposure of a subject to cyanide, comprising the steps of: obtaining a sample from the subject; contacting the sample with a cobinamide conjugate comprising a cobinamide moiety and a carrier; measuring the absorbance of light by the cobinamide conjugate; and determining the presence or absence of cyanide in the sample, or the amount of cyanide in the sample. In one embodiment, the presence of cyanide in the sample indicates exposure of the subject to cyanide. In one aspect, the method further comprises comparing the amount of cyanide in the sample with a control feature, wherein an amount of cyanide in the sample higher than the control feature indicates exposure of the subject to cyanide. In some embodiments, the instant invention provides a method for determining exposure of a subject to cyanide in accordance with any combination of the preceding embodiments.

BRIEF DESCRIPTION OF THE DRAWINGS

FIG. 10 shows representative steps of a field-deployable, rapid cyanide test. Step 1: Adsorb finger-stick blood sample into sponge impregnated with the cobinamide-conjugate. Step 2: Squeeze tube containing lysis reagent to release buffer, and then mix the buffer, blood and cobinamide-conjugate. Step 3: Insert collection tube into test device, and sample flows through filter to remove cellular debris, etc., through membrane coated with capture reagent (streptavidin). Step 4: Incubate and slide sample tube holder/optical module over capture zone. Step 5 can be any of the following scenarios 5a- 5c. Step 5a: Digital readout displays result as "negative" for cyanide. Step 5b: Digital readout displays result as "low positive" for cyanide. Step 5c: Digital readout displays result as "positive" for cyanide.

DETAILED DESCRIPTION OF THE INVENTION

Figure 1:
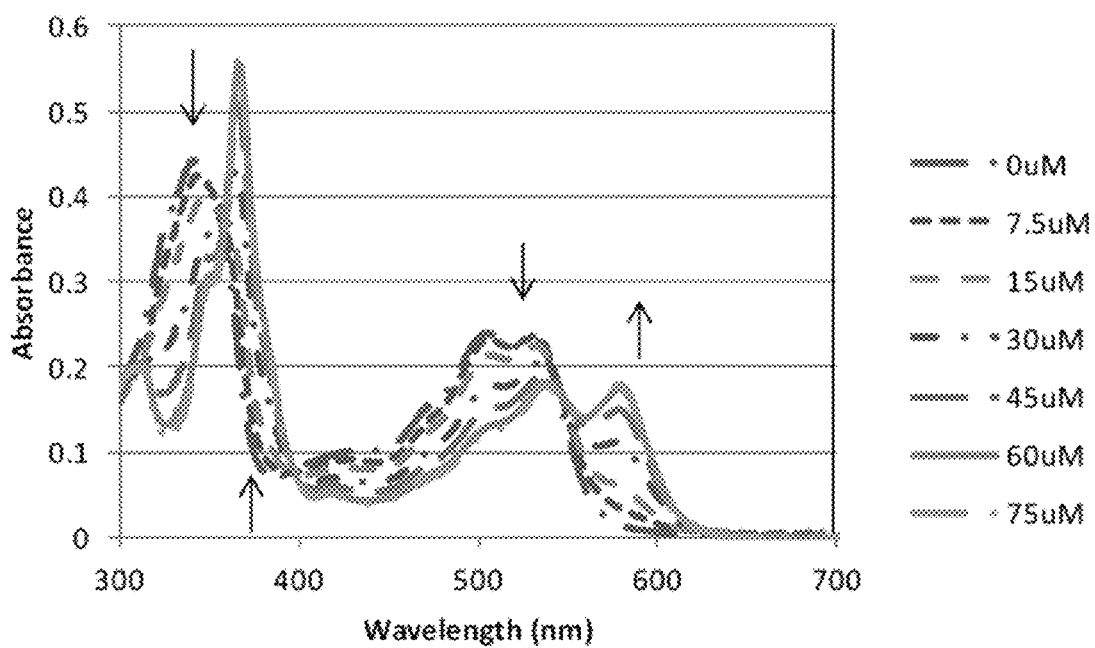
FIG. 1 shows the spectral change of cobinamide on adding cyanide. UV-visible spectrum of a 50 μM cobinamide solution in 60 mM NaOH using a 1 cm path-length cuvette, when cyanide concentration is 0 μM, is shown. Increasing cyanide concentrations ranging from 7.5 μM to 75 μM were added to the cobinamide solution to generate the spectra. The spectral shift causes a marked color change from orange (505 nm and 531 nm peaks) to pink (583 nm peak). Cyanide concentrations tested: 7.5 μM, 15 μM, 30 μM, 45 μM, 60 μM, and 75 μM.

Unless defined otherwise, all terms of art, notations and other technical and scientific terms or terminology used herein are intended to have the same meaning as is commonly understood by one of ordinary skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All publications, including patent documents, scientific articles and databases, referred to in this application and the bibliography and attachments are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims. In the following description of certain embodiments provided here, reference is made to the accompanying drawings which form a part hereof, and in which it is shown by way of illustration specific embodiments in which the invention can be practiced. It is to be understood that other embodiments can be used and structural changes can be made without departing from the scope of the invention.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, "a" or "an" means "at least one" or "one or more."

"Individual" means any living organism, including humans and other mammals.

By "subject" is meant an organism to which the provided compositions, methods, kits, and devices can be administered or applied. In one embodiment, the subject is a mammal or a cell, a tissue, an organ or a part of the mammal. Mammals include, but are not limited to, humans and non-human animals, including farm animals, sport animals, rodents and pets.

As used herein, a "composition" refers to any mixture of two or more products or compounds. It may be a solution, a suspension, liquid, powder, a paste, aqueous, non-aqueous or any combination thereof.

Cyanide is a potent blood agent which is very volatile and is also soluble in water as hydrogen cyanide (HCN) or cyanogen chloride (CNCl). Cyanide rapidly inhibits cellular respiration and can be lethal either by inhalation or oral intake. Cyanide acts extremely rapidly and can cause death within minutes. It has multiple mechanisms of toxicity, with its primary target mitochondrial cytochrome c oxidase in the electron transport chain (Way, 1984, Annu. Rev. Pharmacol. Toxicol. 24: 451-481). It can be inhaled or absorbed across the skin as cyanide gas or ingested as a cyanide salt, e.g., sodium or potassium cyanide. There is need to develop methods for rapid field based cyanide poisoning diagnostics, because of the rapid lethality of cyanide. In one aspect, the present invention discloses methods for rapid field based cyanide detection. In other aspects, the present invention is concerned with determining the exposure to cyanide, the curative treatment of cyanide poisoning, cyanide antidote therapy, and the expense and dosing thereof.

Without being bound by any theory, a cyanide as used herein is a chemical compound that contains the cyano group, —C≡N, which consists of a carbon atom triple-bonded to a nitrogen atom. A cyanide as used herein includes but should not be interpreted as limited to hydrogen cyanide, hydrocyanic acid gas dissolved in a liquid medium, cyanide compound such as a salt of the polyatomic anion $CN^-$, or a dissolved cyanide compound such as sodium cyanide and potassium cyanide in a liquid medium. In certain embodiments, analyses of cyanide amount using the method, kit, or device described herein are performed at a pH above the pKa of cyanide. This minimizes loss of the cyanide to be measured as a gas, leading to more accurate analysis. This also is safer for those performing the analysis if the amount of cyanide to be detected is at a dangerously high level.

Blood cyanide levels for healthy persons have been reported as being ≈0.3 μM using a gas chromatography method (Ishii et al., 1998, Anal. Chem., 70(22): 4873-4876), with lethal cyanide blood levels for fire victims in the cyanide concentration range 23-26 μM (Ishii et al., 1998, Anal. Chem., 70(22): 4873-4876; Moriva and Hashimoto, 2001, J. For. Sci., 46(6): 1421-1425), some two orders of magnitude higher than normal healthy blood levels.

Provided herein are assays, methods, kits and devices for detecting cyanide, particularly in biological/physiological samples. Compared to the methods disclosed herein, some methods in the art require multistep sample pre-treatment procedures, which are laborious and time-consuming. Potentiometric sensor systems have been advocated, but suffer from the problems of response instability, inadequate sensitivity, and interference from thiocyanate. Interference from thiocyanate precludes the use of potentiometric sensor systems in blood and saliva. Some other approaches require expensive and bulky laboratory-based equipment and are not suitable for clinical or field use. Cyanide-sensitive test paper has been developed for use at point of contact; however, the method has low sensitivity (LOD 40 μM), and thiocyanate interferes with the assay.

Cobinamide, the penultimate precursor in the biosynthesis of cobalamin (vitamin $B_{12}$), has an extremely high affinity for cyanide and undergoes a characteristic spectral shift when cyanide is bound to the molecule. Disclosed herein are cyanide-measuring devices based on the very high binding affinity of cobinamide for cyanide and its spectral shift. At pH >11, cobinamide exists as dihydroxycobinamide which has the structure of:

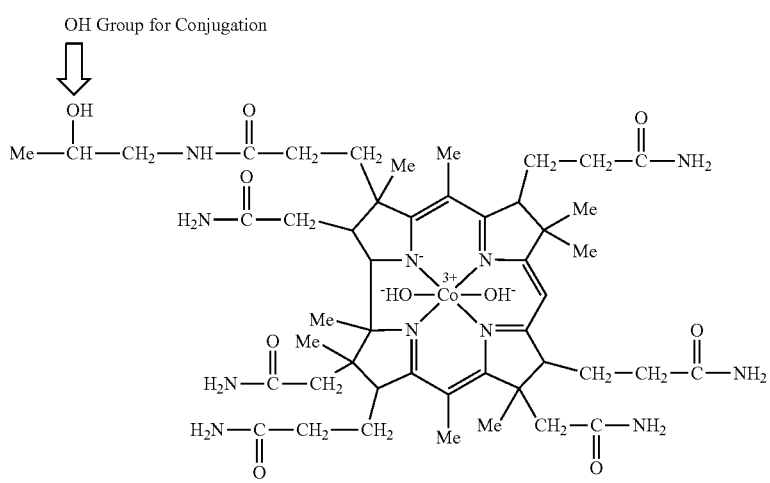

At neutral pH, cobinamide exists as hydroxyaquocobinamide in which one of the two hydroxyl groups bound to the $Co^{3+}$ of the dihydroxycobinamide is replaced by a water. At acidic pH, cobinamide exists as diaquocobinamide in which the remaining hydroxyl group bound to the $Co^{3+}$ of the hydroxyaquocobinamide is replaced by a second water. The term cobinamide as used herein includes diaquocobinamide, hydroxyaquocobinamide and diaquocobinamide. Without being bound by any theory, other cobinamide-containing compound or cobinamide derivative which essentially retains the function to bind cyanide and undergo a characteristic spectral shift, can be used for the practice of the present disclosures. For example, monocyanocobinamides, including any cobinamide in which one of the coordination positions around cobalt is taken by a cyanide ion, can be used. Similarly, monocyanocobinamides can exist in the forms of aquocyanocobinamide and hydroxycyanocobinamide, among other forms.

Cobinamide can be obtained by any suitable methods known to one of skill in the art, including acid hydrolysis methods and base hydrolysis methods. For example, acid hydrolysis of cobalamin can be used (Broderick et al., 2005, J Biol. Chem. 280: 8678-8685). Base hydrolysis of hydroxocobalamin can also be used to produce cobinamide (Renz, 1971, Methods Enzymol. 18: 82-86).

Cobinamide is highly water soluble, and undergoes a dramatic spectral and color change on binding cyanide (FIG. 1). The two coordination positions on cobalt in cobinamide that variously have water or hydroxyl groups, depending on pH, bind cyanide. Cobinamide has a characteristic spectral shift in solutions, including in plasma and in whole blood, when cyanide is added. Cobinamide binds two cyanide ions, the first with a $K_A$ of $>10^{14}$ $M^{-1}$ and the second with a $K_A$ of about $10^8$ $M^{-1}$, leading to a $K_A$ overall of $>10^{22}$ $M^{-2}$. The $10^{22}$ $M^{-2}$ value is an enormously high association constant, similar to chelating agents (Boehringer et al., 2012, "A field-deployable device for the rapid detection of cyanide poisoning in whole blood," SPIE Proceedings Vol. 8371). Cobinamide undergoes a greater absorbance change than does any of the cobalamins and can thus be used for sensitive photometric measurement of cyanide, down to low µM levels. In certain embodiments, a color change is used to rapidly identify clinically relevant cyanide concentrations in biological samples, such as blood. In one aspect, the spectral shift causes a marked color change from the peaks at about 505 nm and about 531 nm to the peak at about 583 nm. In one aspect, the color change is from orange to pink. In certain aspect, the color change is from orange to purple. In some embodiments, changes in single wavelengths, wavelength ratios, and wavelength range models are used to accurately measure cyanide in samples, in particular physiological or biological samples.

In one embodiment, disclosed herein is a cobinamide conjugate comprising a cobinamide moiety and a carrier. The carrier can be a molecule, particle, composition, or other microscopic object to which may be conjugated, directly or indirectly, at least one cobinamide moiety, and in some embodiments, a multiplicity of cobinamide moieties, so as to form a cobinamide conjugate. In certain embodiments, the carrier refers to the backbone of the conjugate, on which various molecules may be attached. In particular examples, the carrier comprises water-soluble polymers, including but are not limited to natural and synthetic polysaccharides, as well as derivatives thereof, for example dextrans and dextran derivatives, starches and starch derivatives, cellulose derivatives, amylose and pectin, as well as certain natural gums and derivatives thereof, such as gum arabic and salts of alginic acid; homopoly(amino acid)s having suitable reactive functionalities, such as polylysines, polyhistidines or polyornithines; natural and synthetic polypeptides and proteins, such as bovine serum albumin, immunoglobulins, and other mammalian albumins; and synthetic polymers having nucleophilic functional groups, such as polyvinyl alcohols, polyallyl alcohol, polyethylene glycols and substituted polyacrylates.

In certain embodiments, the carrier is a molecule, such as a polypeptide. In certain embodiments, the carrier molecule is biotinylated or can be otherwise modified for use in the present invention. In one aspect, the polypeptide is a polylysine or an immunoglobulin.

In other embodiments, the carrier is a surface. The surface can be a plastic surface, or a surface comprised in a nitrocellulose membrane, a nylon membrane, a latex particle, or a gold particle.

In some embodiments, the cobinamide conjugate is particulate, the carrier is biodegradable, the carrier is non-immunogenic, the carrier has a net neutral or negative charge, and/or the carrier is fluorescently labeled. The carrier may be covalently or non-covalently bound to a surface, such as a plastic surface, or a surface comprised in a nitrocellulose membrane, a nylon membrane, a latex particle, or a gold particle.

In some embodiments, the cobinamide conjugate comprises a carrier which is a substantially spherical bead or a porous bead. In certain embodiments in which the carrier is a bead, the bead preferably comprises a material selected from the group consisting of glass, silica, polyesters of hydroxy carboxylic acids, polyanhydrides of dicarboxylic acids, or copolymers of hydroxy carboxylic acids and dicarboxylic acids.

In some embodiments, the cobinamide conjugate comprises a carrier which is a branched polymer, such as a dendrimer. In preferred embodiments when the carrier is a dendrimer, the dendrimer comprises a material selected from the group consisting of a polyamidoamine, a polyamidoalcohol, a polyalkyleneimine, a polyalkylene, a polyether, a polythioether, a polyphosphonium, a polysiloxane, a polyamide, and a polyaryl polymer.

In some embodiments, the cobinamide conjugate further comprises a linker. A linker can be a bi-functional molecule capable of establishing covalent links between other molecules. Examples of bi-functional molecules suitable as linkers include but are not limited to glutaraldehyde, carbodiimides, N,N'-phenylenedimaleimide, N-succinimidyl 3-(2-pyridylthio)propionate, p-benzoquinone, divinyl sulfone (DVS) and epoxide derivatives such as epichlorohydrin and other epoxide derivatives described in U.S. Pat. No. 6,627,460, incorporated herein by reference. Preferably, the linking component should be stable in an aqueous environment.

In some embodiments, the cobinamide conjugate further comprises a spacer. A spacer can be a protein or a polypeptide having a plurality of sites available for covalent attachment of other components. Although not necessary for practicing the invention, a spacer may provide a suitable means of increasing the number of cobinamide moieties which can be attached to the conjugate, thereby increasing the sensitivity of such conjugates when employed in various assays.

Examples of protein spacers include but are not limited to bovine serum albumin, ovalbumin, globulin, etc. Examples of polypeptide spacers include but are not limited to homopolypeptides, such as polylysines, polyhistidines, polyornithines, etc. As will be clear to a person skilled in the art, the choice of spacer will depend on the employed cobinamide moiety, the employed carrier, as well as the employed linking component. In some aspects, the spacer component can be a polysaccharide or polynucleic acid. Chemical modifications of these polymers may be required prior to the preparation of the water-soluble intermediate conjugate.

In one aspect, the cobinamide conjugate comprises a multiplicity of cobinamide moieties. In one embodiment, the cobinamide moiety is conjugated to the carrier via a non-covalent interaction. In another embodiment, the cobinamide moiety is conjugated to the carrier covalently.

Whatever the carrier is and whichever the method used for conjugation is, the cobinamide conjugate disclosed herein essentially retains the ability to bind cyanide and the spectral characteristics of cobinamide upon binding cyanide.

In some preferred embodiments, the cobinamide conjugate is immobilized on a surface, either directly or indirectly. The immobilization method can be a chemical method, catalyzed by an enzyme, or catalyzed a suitable catalyst. The surface can be a plastic surface, or a surface comprised in a bead, a nitrocellulose membrane, a nylon membrane, a latex particle, or a gold particle. In certain embodiments, the surface comprises a material selected from the group consisting of glass, silica, polyesters of hydroxy carboxylic acids, polyanhydrides of dicarboxylic acids, or copolymers of hydroxy carboxylic acids and dicarboxylic acids.

Without being bound by any theory, the cobinamide moiety can be conjugated to the carrier at any suitable position of the cobinamide moiety to form the cobinamide conjugate. In one aspect, the cobinamide moiety is conjugated to the carrier by a covalent bond involving the OH group of the cobinamide moiety. As used herein, the OH group for conjugating the cobinamide moiety to the carrier, either directly or indirectly, is the OH group indicated above in the dihydroxocobinamide structure. In one embodiment, the covalent bond is between the OH group of the cobinamide moiety and a nucleophilic group. In one embodiment, the nucleophilic group is the $NH_2$ group of a polylysine. In certain aspects, the OH group of the cobinamide moiety is activated by carbodiimadizole to form the covalent bond. The structure of the cobinamide is such that the $NH_2$ groups of the cobinamide are not reactive to the activated OH. One of skill in the art would understand other diimidazole or other crosslinkers can be used.

In another aspect, the covalent bond is between the OH group of the cobinamide moiety and an isocyanate moiety. The isocyanate moiety can be comprised in N-[p-maleimidophenyl]isocyanate (PMPI). The isocyanate moiety of PMPI reacts with the OH group of the cobinamide, leaving the maleimide moiety of PMPI available to react with an available sulfhydryl group. In one aspect, the maleimide moiety of PMPI forms a covalent bond with a sulfhydryl group, which in certain embodiments, can be comprised in the carrier. Sulfhydryl groups can be introduced to molecules such as polylysine and bovine serum albumin through the use of N-Succinimidyl S-Acetylthioacetate (SATA) and other similar molecules. The succinimide group of the SATA reacts with primary amines and leaves a S-acetylthioacetic acid group. Removing the acetyl group leaves a sulfhydryl group that is then reacted with maleimide group introduced to the cobinamide. In one aspect, excess reactants are removed before the cobinamide conjugate is used to detect cyanide.

In yet another aspect, the isocyanate moiety is comprised in a molecule comprising a multiplicity of $NH_2$ groups each capable of reacting with an activated ester. In certain embodiments, particles containing surface carboxylic acid groups are activated with N-(3-dimethylaminopropyl)-N'-ethylcarbodiimide (EDC) and N-hydroxysuccinimide (NHS) which convert a carboxylic acid group to an active ester. The active ester on the particles are then reacted with the terminal $NH_2$ of poly Tyrosine or poly-tyrosine which have multiple OH groups. The OH groups of the poly-Tyrosine/threonine are reacted with a large excess of hexamethylene diisocyanate to introduce a reactive isocyanate to each OH of the poly Tyrosine/threonine. Excess reactants are removed and the isocyanate group is then reacted with the OH group on the cobinamide. In certain aspects, a multiplicity of the activated esters are comprised in a molecule, a particle, or a surface. In certain embodiments, a multiplicity of cobinamide moieties are conjugated to a multiplicity of activated esters comprised in a molecule, particle, or surface.

In the preferred embodiments, the cobinamide conjugate retains the characteristic spectral shift of cobinamide upon binding cyanide, both when the cobinamide conjugate is in solution and when it is immobilized on a molecule, particle, or surface.

Also provided herein is a method for cyanide detection, comprising contacting a sample with a cobinamide conjugate comprising a cobinamide moiety and a carrier, and measuring the absorbance of light by the cobinamide conjugate.

In some aspects, measuring the absorbance of light by the cobinamide conjugate is performed at a single wavelength. In some embodiments, the method disclosed herein further comprises comparing the absorbance of light by the cobinamide conjugate with a control feature. In certain embodiments, the absorbance of light is measured and compared with a reference or background. In certain aspects, the reference or background is measured at a wave length greater than 650 nm. In other aspects, the reference or background is measured at a wave length of about 650 nm. In spectroscopy, an isosbestic point is a specific wavelength at which two chemical species have the same molar absorptivity or, more generally, are linearly related. In some embodiments, the method disclosed herein further comprises using an isosbestic point for corrections of minor variations in cobinamide amounts.

In one aspect, the absorbance of light in the method disclosed herein is measured at a visible wavelength. In certain embodiments, the absorbance of light is measured at a wavelength of about 400 nm to about 700 nm. In certain aspects, the absorbance of light is measured at a wavelength of about 400 nm to about 500 nm, about 500 nm to about 600 nm, or about 600 nm to about 700 nm. In one aspect, the wavelength used is of about 500 nm to about 520 nm, preferably of about 500 nm to about 510 nm, and more preferably of about 505 nm. In another aspect, the wavelength used is of about 520 nm to about 540 nm, preferably of about 525 nm to about 535 nm, and more preferably of about 531 nm. In certain aspects, the wavelength used is of about 540 nm to about 560 nm, or of about 560 nm to about 580 nm. In another aspect, the wavelength used is of about 580 nm to about 600 nm, preferably of about 580 nm to about 590 nm, and more preferably of about 583 nm.

In another aspect, the absorbance of light in the method disclosed herein is measured at an invisible wavelength. In certain embodiments, the absorbance of light is measured at a wavelength of about 250 nm to about 400 nm. In certain aspects, the absorbance of light is measured at a wavelength of about 250 nm to about 300 nm, about 300 nm to about 350 nm, or about 350 nm to about 400 nm. In one aspect, the wavelength used is of about 350 nm to about 400 nm, preferably of about 360 nm to about 380 nm, more preferably of about 360 nm to about 370 nm, and even more preferably of about 366 nm.

In certain embodiments, the method disclosed herein detects the presence or absence of cyanide in a sample. In one aspect, the method detects the amount of cyanide in the sample quantitatively. In one other aspect, the method detects the amount of cyanide in the sample qualitatively. Both the quantitative and the qualitative aspects of the method have a high throughput capacity, or can be adapted for use in throughput measurement.

For quantitative measurement, a spectrophotometer can be used. In some preferred embodiments, commercially available discrete LEDs centered at each of these wavelengths can be used. In certain aspect, narrow band interference filters are used and these LED light sources are essentially monochromatic. Other light sources commonly used with spectrophotometry can also be used, including lasers. In certain aspect, the method further comprises using a detector. A detector can be a charge-coupled device (CCD), a photodiode array, or other light sensors suitable for detecting the spectral shift.

For quantitative measurement, visual observation of the color change in the sample can be used. In certain embodiments, the color change is from orange to pink. In certain embodiments, the color change is from orange to purple.

In certain embodiments, the method disclosed herein detects the presence or absence of cyanide in a biological sample. Biological samples as used herein can encompass matter or material which contains matter that is originally of biological origin, including sample of biological tissue or fluid origin obtained in vivo or in vitro. Such samples can be, but are not limited to, body fluid (e.g., saliva, whole blood, blood plasma, serum, lymph, synovial fluid, peritoneal fluid, pleural fluid, urine, sputum, semen, vaginal lavage, bone marrow, cerebrospinal cord fluid and tears), organs, tissues, fractions and cells isolated from mammals including, humans. These original biological samples may be further aliquoted or divided into multiple biological samples. The biological sample may for instance be material entirely taken from an organism or it may be matter which is taken from an organism and is processed possibly being mixed with other material. For instance a blood or urine sample may be mixed with a preservative or a solvent or diluted. The biological sample also encompasses biological material which has been broken down or processed with chemicals such as enzymes or other materials for changing the chemical structure of the biological sample. Biological samples may be dispersed in solution or may be immobilized on a solid support, such as in blots, assays, arrays, glass slides, microtiter, or ELISA plates.

The method, kit and device disclosed herein can be used in tests for cyanide to provide a rapid readout, either qualitatively or quantitatively. In certain embodiments, the test has an assay time of about 1 minute to about 30 minutes, from sample collection to a valid result. In some embodiments, the test has an assay time of about 1 minute to about 5 minutes, about 5 minutes to about 10 minutes, about 10 minutes to about 15 minutes, about 15 minutes to about 20 minutes, about 20 minutes to about 25 minutes, or about 25 minutes to about 30 minutes. In preferred embodiments, the test has an assay time of less than 5 minutes, from sample collection to a valid result. In some aspects, the test has an assay time of about 1 minute, about 2 minutes, about 3 minutes, about 4 minutes, or about 5 minutes. In preferred embodiments, the test provides a rapid result of the cyanide level in the sample at the point of collection.

In certain embodiments, the sample is contacted with the cobinamide conjugate without any pre-treatment. In certain other embodiments, the sample is treated before, after, or at about the same time when the sample is contacted with the cobinamide conjugate. In one aspect, the sample is a blood sample. In one embodiment, the blood sample is treated to remove red blood cells. Without being bound by any theory, the treatment to remove red blood cells can be performed before, after, or at about the same time when the sample is contacted with the cobinamide conjugate.

It has been demonstrated that whole blood or components thereof, including hemoglobin, interfere with the wavelength shift of cobinamide. Cobinamide has an extremely high affinity for cyanide and captures hemoglobin associated cyanide from red blood cells. In preferred embodiments, blood separation and/or removal of hemoglobin to eliminate this interference is required. The device described herein includes various methods to remove red blood cells (intact or lysed) and other blood components.

The inventors of the present invention have shown a field-deployable device can be used for the rapid and early diagnosis of cyanide poisoning in whole blood using the spectral shift of the vitamin $B_{12}$ precursor cobinamide upon binding with cyanide as an indicator. The present inventors have combined cyanide-binding properties of cobinamide with blood separation technology, sample transport technology and a detection system, and have developed a rapid, field deployable, disposable device which delivers an intuitive result to a first responder, allowing for rapid response to exposure events. In one embodiment, the intuitive result is qualitative. In certain aspects, the intuitive result indicates the presence or absence of cyanide in the blood sample. In one aspect, the intuitive result involves a color change from the peaks at about 505 nm and about 531 nm to the peak at about 583 nm. In one aspect, the color change is from orange to pink. In one aspect, the color change is from orange to purple. In another embodiment, the intuitive result is quantitative. In certain aspects, the intuitive result indicates the amount of cyanide in the blood sample.

In some embodiments, the method or device disclosed herein is used in a rapid test using a whole blood sample. The whole blood sample can be collected by any method known to one of skill in the art. In a preferred embodiment, the whole blood sample is collected from a finger-stick. In certain embodiments, the test has an assay time of about 1 minute to about 30 minutes, from sample collection to a valid result. In some embodiments, the test has an assay time of about 1 minute to about 5 minutes, about 5 minutes to about 10 minutes, about 10 minutes to about 15 minutes, about 15 minutes to about 20 minutes, about 20 minutes to about 25 minutes, or about 25 minutes to about 30 minutes. In preferred embodiments, the test has an assay time of less than 5 minutes, from sample collection to a valid result. In some aspects, the test has an assay time of about 1 minute, about 2 minutes, about 3 minutes, about 4 minutes, or about 5 minutes.

Blood cyanide levels for healthy persons have been reported as being ≈0.3 μM using a gas chromatography method (Ishii et al., 1998, Anal. Chem., 70(22): 4873-4876). In preferred embodiments, the method disclosed herein detects in a sample physiologically relevant amounts of cyanide. Without being bound by any theory, in certain embodiments, the method disclosed herein detects in a sample cyanide amount in the range of about 0.05 μM to about 0.1 μM, about 0.1 μM to about 0.2 μM, about 0.2 μM to about 0.4 µM, about 0.4 µM to about 0.8 µM, about 0.8 µM to about 1.6 µM, about 1.6 µM to about 3.2 µM, about 3.2 µM to about 6.4 µM, about 6.4 µM to about 12.8 µM, or about 12.8 µM to about 25.6 µM. In some embodiments, the method detects cyanide amounts in the range of about 25 µM to about 30 µM, about 30 µM to about 35 µM, about 35 µM to about 40 µM, about 45 µM to about 50 µM, about 55 µM to about 60 µM, about 65 µM to about 70 µM, about 75 µM to about 80 µM, about 85 µM to about 90 µM, or about 95 µM to about 100 µM. In some other embodiments, the method detects cyanide amounts of about 100 µM. In some aspects, the method detects cyanide levels above 100 µM. In some aspects, the method detects cyanide levels of about 150 µM, about 200 µM, about 250 µM, about 300 µM, about 350 µM, about 400 µM, 450 µM, about 500 µM, about 550 µM, about 600 µM, about 650 µM, about 700 µM, 750 µM, about 800 µM, about 850 µM, about 900 µM, about 950 µM, or about 1000 µM. In some other embodiments, the method detects cyanide amounts above 1000 µM.

In yet another aspect, provided herein is a kit for detecting cyanide in a sample, comprising a cobinamide conjugate, said cobinamide conjugate comprising a cobinamide moiety and a carrier. In one embodiment, the kit further comprises a composition for sample collection. In another embodiment, the kit further comprises a composition for sample processing. In yet another embodiment, the kit further comprises a composition for capturing the cobinamide conjugate.

In certain embodiments, the carrier is a molecule, such as a polypeptide. In certain embodiments, the carrier molecule is biotinylated or can be otherwise modified for use in the present invention. In one aspect, the polypeptide is a polylysine or an immunoglobin. Without being bound by any theory, the carrier and the cobinamide conjugate can be in the form as described in any embodiment or example of this invention. In certain embodiments, the composition for sample collection can be a sponge, a paper, and a porous membrane. Other compositions suitable for the purpose of the present invention can also be used. In some embodiments, the composition for sample collection further comprises the cobinamide conjugate. In some embodiments, the composition for sample processing comprises a lysis reagent or an enzyme. In one aspect, the composition for sample processing is a buffer or a solution.

In other embodiments, the composition for capturing the cobinamide conjugate is comprised in a surface. The surface can be a plastic surface, or a surface comprised in a nitrocellulose membrane, a nylon membrane, a latex particle, or a gold particle. In one embodiment, the composition for capturing the cobinamide conjugate of the invention is capable of capturing a multiplicity of the cobinamide conjugates.

In yet another aspect, provided herein is a device for detecting cyanide in a sample, comprising a chamber for housing a cobinamide conjugate, said cobinamide conjugate comprising a cobinamide moiety and a carrier. In one embodiment, the device further comprises a detector, wherein the detector detects the absorbance of light by the cobinamide conjugate. In some embodiments, the device further comprises a display indicating the presence or absence of cyanide in the sample, or the amount of cyanide in the sample.

In some embodiments, the device further comprises a second chamber for sample collection, wherein the second and first chambers can be the same or different. The chamber for sample collection can comprise a material impregnated with the cobinamide conjugate. In some embodiments, the material impregnated with the cobinamide conjugate can be a sponge, a paper, and a porous membrane. Other materials suitable for the purpose of the present invention can also be used.

In some embodiments, the device further comprises a third chamber for housing a composition for sample processing. In one aspect, the device further comprises a means for separating the cobinamide conjugate from the sample after processing. In one embodiment, the device further comprises a means for capturing the cobinamide conjugate. In one aspect, the means for capturing the cobinamide conjugate can be a surface adapted to allow measurement of the absorbance of light by the captured cobinamide conjugate. Such a surface can be comprised in a membrane or particle, for example, a nitrocellulose membrane, a nylon membrane, a latex particle, or a gold particle.

In yet another aspect, provided herein is a method for determining exposure of a subject to cyanide, comprising the steps of: obtaining a sample form the subject; contacting the sample with a cobinamide conjugate comprising a cobinamide moiety and a carrier; measuring the absorbance of light by the cobinamide conjugate; and determining the presence or absence of cyanide in the sample, or the amount of cyanide in the sample. In one embodiment, the presence of cyanide in the sample indicates exposure of the subject to cyanide. In one aspect, the method further comprises comparing the amount of cyanide in the sample with a control feature, wherein an amount of cyanide in the sample higher than the control feature indicates exposure of the subject to cyanide.

The following exemplary embodiments and examples are intended to further describe and illustrate various aspects of the invention, but not to limit, the scope of the invention in any manner, shape, or form, either explicitly or implicitly.

The present invention is further illustrated by the following exemplary embodiments:

1. A method for detecting cyanide in a sample, comprising:
    contacting a sample with a cobinamide conjugate comprising a cobinamide moiety and a carrier; and
    measuring the absorbance of light by the cobinamide conjugate.
2. The method of embodiment 1, wherein the carrier is a molecule.
3. The method of embodiment 1 or 2, wherein the carrier is a polypeptide.
4. The method of any one of embodiments 1-3, wherein the carrier is a polylysine.
5. The method of any one of embodiments 1-4, wherein the carrier is an immunoglobin.
6. The method of any one of embodiments 1-5, wherein the carrier is biotinylated.
7. The method of embodiment 1, wherein the carrier is a surface.
8. The method of embodiment 1 or 7, wherein the carrier is a plastic surface.
9. The method of any one of embodiments 1-8, wherein the carrier is comprised in a nitrocellulose membrane, a nylon membrane, a latex particle, or a gold particle.
10. The method of any one of embodiments 1-9, wherein the cobinamide conjugate comprises a multiplicity of cobinamide moieties.
11. The method of any one of embodiments 1-10, wherein the cobinamide moiety is conjugated to the carrier via a non-covalent interaction, either directly or indirectly.

12. The method of any one of embodiments 1-10, wherein the cobinamide moiety is conjugated to the carrier covalently, either directly or indirectly.
13. The method of any one of embodiments 1-10 and 12, wherein the cobinamide moiety is conjugated to the carrier by a covalent bond involving the OH group of the cobinamide moiety.
14. The method of embodiment 13, wherein the covalent bond is between the OH group of the cobinamide moiety and a nucleophilic group.
15. The method of embodiment 14, wherein the nucleophilic group is the $NH_2$ group of a polylysine.
16. The method of embodiment 13, where in the OH group of the cobinamide moiety is activated by a crosslinker to form the covalent bond.
17. The method of embodiment 13, wherein the covalent bond is between the OH group of the cobinamide moiety and an isocyanate moiety.
18. The method of embodiment 17, wherein the isocyanate moiety is comprised in N-[p-maleimidophenyl] isocyanate (PMPI).
19. The method of embodiment 18, wherein the maleimide moiety of PMPI forms a covalent bond with a sulfhydryl group.
20. The method of embodiment 19, wherein the sulfhydryl group is comprised in the carrier.
21. The method of embodiment 17, wherein the isocyanate moiety is comprised in a molecule comprising a multiplicity of $NH_2$ groups each capable of reacting with an activated ester.
22. The method of embodiment 21, wherein a multiplicity of activated esters are comprised in a molecule, a particle, or a surface.
23. The method of embodiment 22, wherein a multiplicity of cobinamide moieties are conjugated to the multiplicity of activated esters comprised in the molecule, particle, or surface.
24. The method of any one of embodiments 1-23, which detects the presence or absence of cyanide in the sample.
25. The method of any one of embodiments 1-24, which detects the amount of cyanide in the sample quantitatively.
26. The method of any one of embodiments 1-25, further comprising comparing the absorbance of light by the cobinamide conjugate with a control feature.
27. The method of any one of embodiments 1-26, wherein the absorbance of light is measured at a visible wavelength.
28. The method of embodiment 27, wherein the absorbance of light is measured at a wavelength of about 400 nm to about 700 nm.
29. The method of any one of embodiments 1-25, wherein the absorbance of light is measured at an invisible wavelength.
30. The method of embodiment 29, wherein the absorbance of light is measured at a wavelength of about 250 nm to about 400 nm.
31. The method of any one of embodiments 1-30, wherein the sample is contacted with the cobinamide conjugate without pre-treatment.
32. The method of any one of embodiments 1-31, wherein the sample is a biological sample.
33. The method of embodiment 32, wherein the biological sample is blood.
34. The method of embodiment 33, wherein the blood sample is treated to remove red blood cells.
35. The method of any one of embodiments 1-34, wherein the detection of cyanide is completed in less than five minutes.
36. The method of any one of embodiments 1-35, wherein the amount of cyanide in the sample is from about 25 µM to about 100 µM.
37. A kit for detecting cyanide in a sample, comprising a cobinamide conjugate, said cobinamide conjugate comprising a cobinamide moiety and a carrier.
38. The kit of embodiment 37, further comprising a composition for sample collection.
39. The kit of embodiment 37 or 38, further comprising a composition for sample processing.
40. The kit of any one of embodiments 37-39, further comprising a composition for capturing the cobinamide conjugate.
41. The kit of any one of embodiments 37-40, wherein the carrier is a molecule.
42. The kit of any one of embodiments 37-41, wherein the carrier molecule is a polypeptide.
43. The kit of any one of embodiments 37-42, wherein the carrier is a polylysine.
44. The kit of any one of embodiments 37-43, wherein the carrier is an immunoglobin.
45. The kit of any one of embodiments 37-44, wherein the carrier is biotinylated.
46. The kit of embodiment 40, wherein the composition for capturing the cobinamide conjugate carrier is comprised in a surface.
47. The kit of embodiment 46, wherein the surface is a plastic surface.
48. The kit of embodiment 46, wherein the surface is comprised in a nitrocellulose membrane, a nylon membrane, a latex particle, or a gold particle.
49. The kit of embodiment 40, wherein the composition for capturing the cobinamide conjugate is capable of capturing a multiplicity of the cobinamide conjugates.
50. A device for detecting cyanide in a sample, comprising a chamber for housing a cobinamide conjugate, said cobinamide conjugate comprising a cobinamide moiety and a carrier.
51. The device of embodiment 50, further comprising a detector, wherein the detector detects the absorbance of light by the cobinamide conjugate.
52. The device of embodiment 50 or 51, further comprising a display indicating the presence or absence of cyanide in the sample, or the amount of cyanide in the sample.
53. The device of any one of embodiments 50-52, further comprising a chamber for sample collection, wherein the chamber for sample collection and the chamber for housing a cobinamide conjugate can be the same or different.
54. The device of embodiment 53, wherein the chamber for sample collection comprises a material impregnated with the cobinamide conjugate.
55. The device of embodiment 54, wherein the material impregnated with the cobinamide conjugate is selected from the group consisting of sponge, paper, and porous membrane.
56. The device of any one of embodiments 50-55, further comprising a chamber for housing a composition for sample processing.
57. The device of any one of embodiments 50-56, further comprising a means for separating the cobinamide conjugate from the sample.

58. The device of any one of embodiments 50-57, further comprising a means for capturing the cobinamide conjugate.
59. The device of embodiment 58, wherein the means for capturing the cobinamide conjugate is a surface adapted to allow measurement of the absorbance of light by the captured cobinamide conjugate.
60. The device of embodiment 59, wherein the surface is comprised in a nitrocellulose membrane, a nylon membrane, a latex particle, or a gold particle.
61. A method for determining exposure of a subject to cyanide, comprising: contacting a sample from the subject with a cobinamide conjugate comprising a cobinamide moiety and a carrier;
measuring the absorbance of light by the cobinamide conjugate; and
determining the presence or absence of cyanide in the sample, or the amount of cyanide in the sample.
62. The method of embodiment 61, wherein the presence of cyanide in the sample indicates exposure of the subject to cyanide.
63. The method of embodiment 61, further comprising comparing the amount of cyanide in the sample with a control feature, wherein an amount of cyanide in the sample higher than the control feature indicates exposure of the subject to cyanide.

EXAMPLE 1

Cobinamide Modifications and Conjugations

Conjugation Cobinamide to Mouse IgG

Cobinamide was modified for immobilization by conjugation to a protein, mouse IgG. First, mouse IgG (Equitech Bio, Kerrville, TX, USA) was modified using SATA (Thermo Scientific Pierce, Rockford, Ill., USA) to introduce multiple protected sulfhydryl groups while cobinamide (Univ. California, San Diego, Calif., USA) was modified using PMPI (Thermo Scientific Pierce, Rockford, Ill., USA) to introduce sulfhydryl reactive maleimide groups. Subsequently, modified cobinamide and mouse IgG were conjugated to form a covalently bound complex.

Mouse IgG modification. Mouse IgG was dissolved in the SATA reaction buffer at 10 mg/mL. SATA was dissolved in DMSO at a concentration of about 10-20 mg/ml, which was prepared immediately before use. Mouse IgG and SATA were combined in a glass tube, and were mixed and incubated for 30 minutes at room temperature. The modified mouse IgG was dialyzed with PBS to remove excess SATA, and was stored refrigerated until use.

Cobinamide modification. 5 mg of cobinamide was dissolved in 0.5 ml of DMF to yield a 10 mg/ml solution. 10 mg of PMPI was dissolved in 0.20 ml of DMF to yield a 50 mg/ml solution. The PMPI solution was added to the cobinamide solution at a 5:1 reaction ratio. The reaction was mixed and incubated on rotator for 2 hours at room temperature (protected from light). 50 mg of OH beads (Bangs Laboratories, Inc., Fisher, IN, USA) were diluted in 0.3 ml DMF and the conjugation mixture was added to bind excess PMPI. The mixture was incubated for 2 hours at room temperature, and was then spun to pellet the beads and recover the supernatant. The cobinamide-PMPI was ready for conjugation.

Deacetylation of SATA-mIgG. 0.411 ml (3.0 mg) SATA-IgG was combined with 41 µl deacetylation solution. The reaction was mixed and incubated for 2 hours at room temperature, and was then purified using a 7K Zeba Spin desalting column (Thermo Scientific Pierce, Rockford, Ill., USA) into PBS containing 10 mMEDTA. The deacetylated SATA-mIgG was then used immediately.

Figure 2:
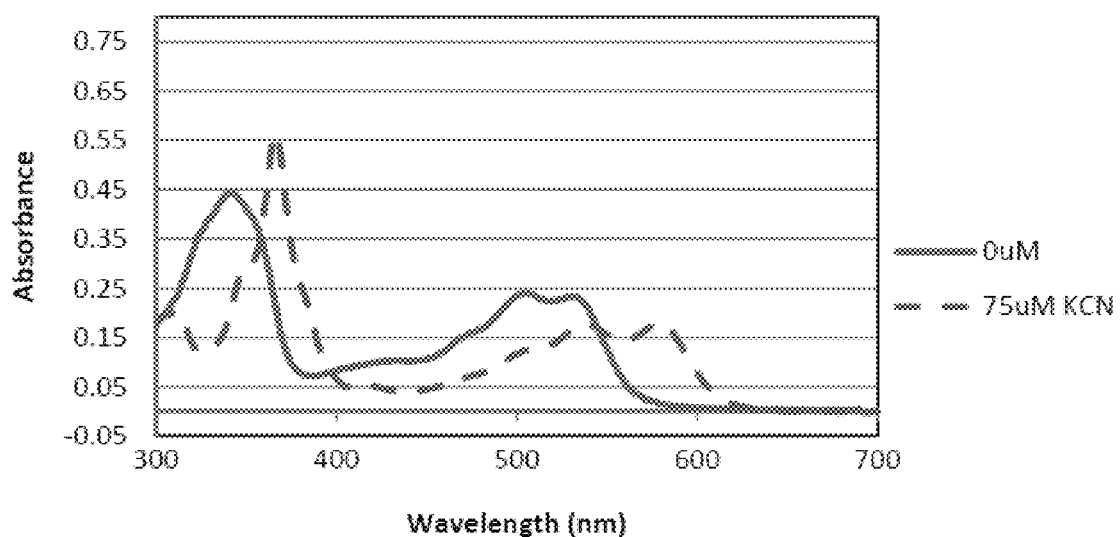
FIG. 2 shows the spectral shift of cobinamide-mouse IgG conjugate on adding 75 μM KCN. The observed spectral shift shows that the conjugated cobinamide is functional post modification.

Cobinamide-IgG conjugation. 2.5 mg of deacetylated SATA-IgG was combined with 120 µl of cobinamide-PMPI at a 50:1 ratio. The mixture was incubated for two hours at room temperature and kept protected from light. The cobinamide-IgG conjugate was ready for use. Evaluation of the conjugate in solution showed that the cobinamide was functional post modification with clear spectral shift when 75 µM KCN was added (FIG. 2).

Conjugation Cobinamide to Polylysine

The preferred method of conjugating cobinamide forms a covalent bond between the OH group of cobinamide and a nucleophilic group of any molecule, in this case the $NH_2$ of polylysine (CAS #25988-63-0, Sigma-Aldrich PN P2636). The terminal OH group of cobinamide was activated by carbodiimadizole (CDI, CAS #530-62-1, Sigma-Aldrich PN 115533) which then reacted with the $NH_2$ groups of the polylysine. The structure of the cobinamide is such that the $NH_2$ groups of the cobinamide are not reactive to the activated OH. Other diimidazole or other crosslinkers can be used in place of carbodiimadizole.

Conjugation Cobinamide to Polytyrosine/Threonine

Cobinamide was conjugated to polytyrosine or polythreonine attached to particles by the following method. Tyrosine and threonine were selected because of the available OH group. Particles with a carboxylic acid active group were modified using N-(3-Dimethylaminopropyl)-N'-ethylcarbodiimide (EDC, CAS #25952-53-8, $C_8H_{17}N_3$, Sigma Chemical PN E6383) and N-Hydroxysuccinimide (NHS, CAS #6066-82-6, $C_4H_5NO_3$, Sigma-Aldrich PN 130672) to convert the COOH groups to NHS-esters. Excess reactants were then removed by centrifuging the particles and removing the supernatant. Polytyrosine (CAS #25619-78-7, Sigma-Aldrich PN P1800) or polythreonine (CAS #30704-25-7, Sigma Aldrich PN P3638) was then added to the activated particles and which reacted with the activated COOH group on the particles via their terminal $NH_2$ group. Excess polytyrosine or polythreonine was then removed by centrifugation. The OH groups of the polytyrosine/threonine were then reacted with a large excess of hexamethylene diisocyanate (CAS #822-06-0, Sigma Aldrich PN 52649) to react with the OH group on the polytyrosine/threonine to create an available isocyanate group. Excess reactants were removed by centrifugation. Finally, cobinamide was added and reacted to the isocyanate group via the terminal OH. Then a suitable interval ethanolamine (TCI America, Cat#A0297) was added to remove any unreacted isocyanate group.

EXAMPLE 2

Cobinamide Measurements- Dry/Immobilized

Cobinamide-mouse IgG conjugate was immobilized onto a nitrocellulose membrane (Whatman Optitran BA-S83; Whatman GE Healthcare Life Sciences, Piscataway, N.J., USA). 5 µl cobinamide-IgG solution were pipeted onto the membrane and dried for 30 minutes at 37° C. 5 µl of a 100 µM KCN solution were directly added onto the immobilized cobinamide-IgG spot. As a control, 5 µl of buffer was added to an adjacent cobinamide-IgG spot. The results of the reaction were recorded after 5 minutes. A change in color from orange to pink/purple was observed.

EXAMPLE 3

Cobinamide Measurements- Liquid

Figure 3:
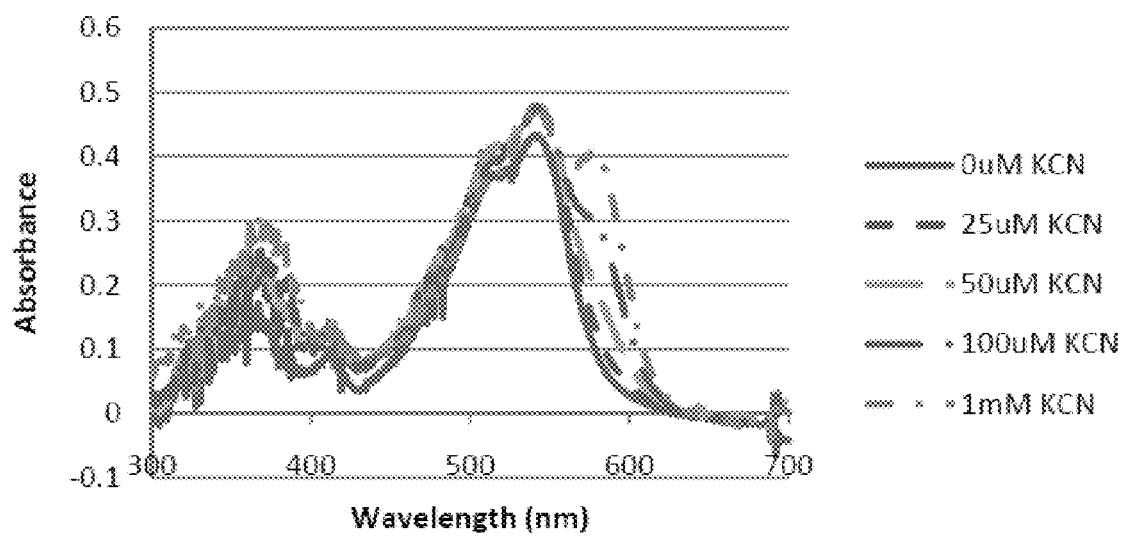
FIG. 3 shows the spectral shift of cobinamide in potassium cyanide (KCN) spiked plasma. The cobinamide (100 μM) was mixed with plasma that contained various levels of potassium cyanide. Wavelength scans in a 1 cm path length cuvette were performed 5 minutes after the potassium cyanide was added. The baseline was adjusted for the 1 mM KCN sample for illustration purposes.
Figure 4:
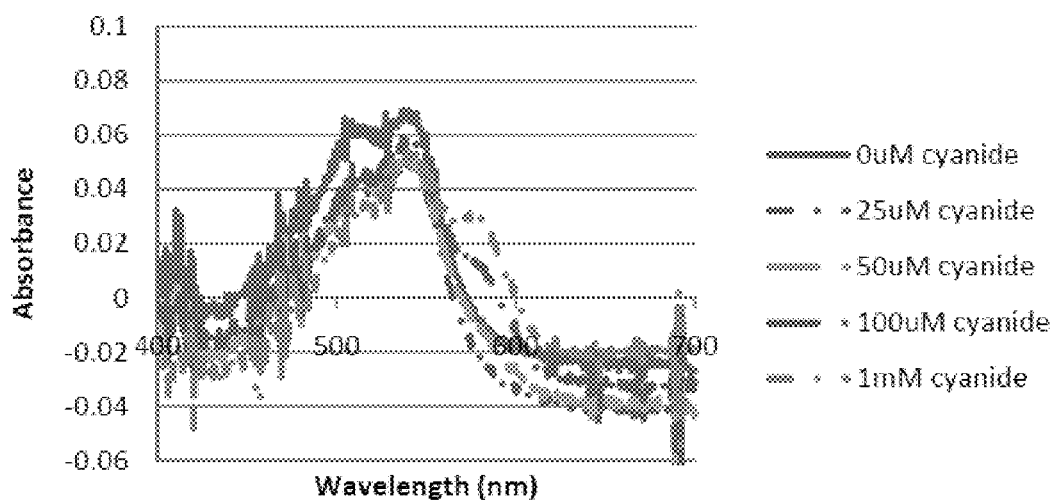
FIG. 4 shows the spectral shift of cobinamide in potassium cyanide (KCN) spiked plasma. The cobinamide (100 μM) was mixed with plasma that contained various levels of potassium cyanide. Wavelength scans in a 0.1 cm path length cuvette were performed 5 minutes after the potassium cyanide was added. The baseline was adjusted for the 1 mM KCN sample for illustration purposes.

Normal human plasma was spiked with 25 µM, 50 µM, 100 µM and 1 mM KCN. 100 µM cobinamide was added to the spiked plasmas, incubated for 5 minutes and read from 400 nm-700 nm on a spectrophotometer using a 1 cm pathlength cuvette (FIG. 3) and a 0.1 cm pathlength microcuvette (FIG. 4).

The peaks at 583 nm increased as the concentration of KCN increased. Use of 1 mm cuvette was noisier than using of 1 cm cuvette, but differences in KCN concentration were still detected.

EXAMPLE 4

Blood Separation

Figure 5:
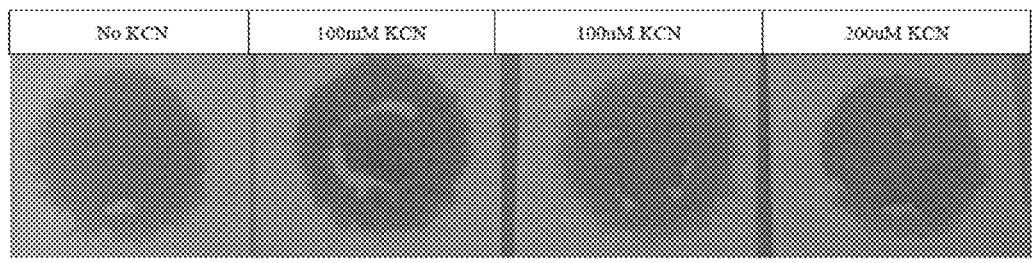
FIG. 5 shows the cobinamide spectral shift in whole blood spiked with potassium cyanide and after red blood cell (RBC) removal. Whole blood was mixed with various concentrations of potassium cyanide and cobinamide. After mixing for 5 minutes, the RBCs were removed and the plasma was captured on a filter. A visible color change was seen with high levels of potassium cyanide only.

Normal whole human blood was spiked with KCN at various concentrations, mixed with cobinamide and incubated for 5 minutes. The blood was filtered through a Pall Vivid GX blood filtration membrane and the resulting plasma was absorbed into a Millipore C083 cellulose pad for detection of color change. A color change can be seen by eye with 200 µM KCN. 100 mM KCN showed a distinct and strong color change (FIG. 5).

EXAMPLE 5

Devices

This example describes representative, non-limiting devices for use in determining the amount of cyanide poisoning in whole blood samples. In this example, the sample is a whole blood sample collected from finger-stick, and is directly applied to the device. Whole blood is rehydrated and mixed with the cobinamide conjugate, and a cobinamide-cyanide complex is formed. Red blood cells are removed without lysis, and the amount of cobinamide-cyanide complex is measured spectrophotometrically. The device is field deployable, with a total assay time of 5 minutes or less. The device is easy to use and to manufacture, compact, and field-deployable, and meets the performance requirements with regard to sensitivity, specificity and assay time.

Figure 6:
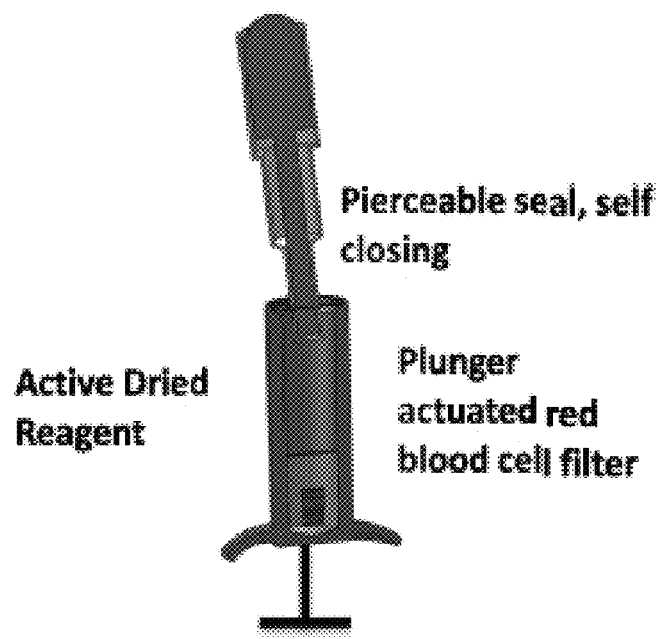
FIG. 6 shows a representative sealed vessel with dried active reagent and vertical red blood cell filter.

A sealed vessel with dried active reagent and vertical red blood cell filter can be used (FIG. 6). User collects finger-stick whole blood sample with capillary dispenser systems and delivers to dried reagent. When the sample delivery plunger is removed and disposed of, the seal closes. User then shakes the contents. The filter plunger is depressed and the plasma/reagent mix collects in the lower chamber. The lower chamber is then inserted into a reader to interpret results.

Figure 7:
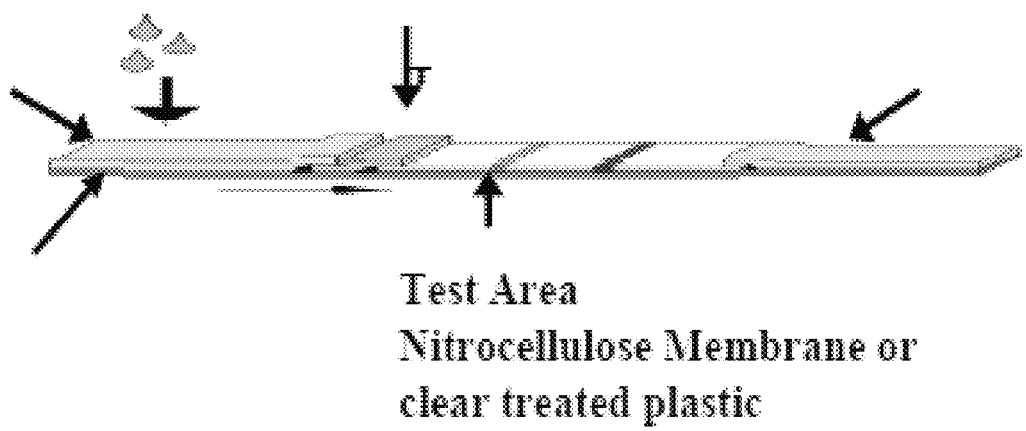
FIG. 7 shows a representative lateral flow-type device with dried active reagent and red blood cell separator.

A lateral flow-type device with dried active reagent and red blood cell separator can be used (FIG. 7). User collects finger-stick whole blood sample with capillary dispenser systems and adds the sample to the sample pad. The sample then mixes with the active reagent in the application pad. The sample and the rehydrated reagent then move together through the whole blood separation pad, which may require an integrated buffer delivery system. Plasma is analyzed in the read area using a low cost field based spectrometer.

Figure 8:
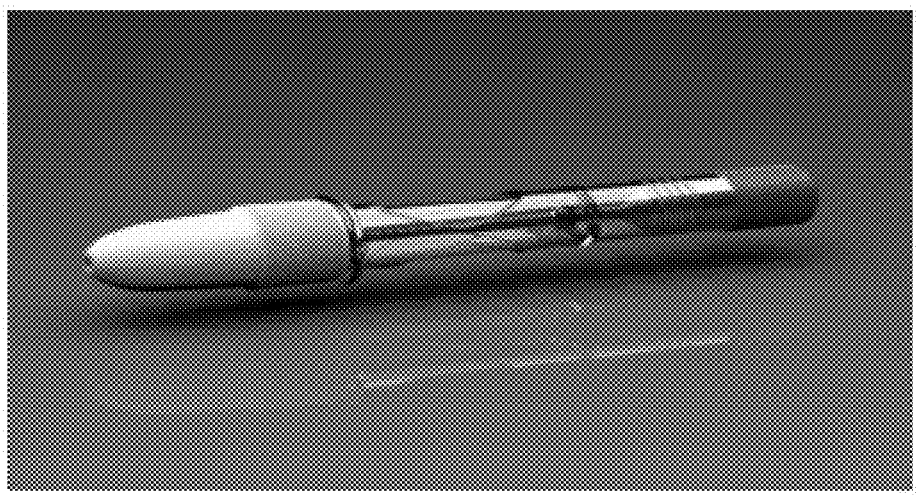
FIG. 8 shows a representative fluid phase system.

A fluid phase system can be used (FIG. 8). The sample is collected into a capillary device with an integrated lancet. The device lid contains buffer that forces sample from the capillary into a mixing chamber containing a lyophilized reagent. A whole blood filter then separates plasma, which is read in miniaturized spectrometer.

Figure 9:
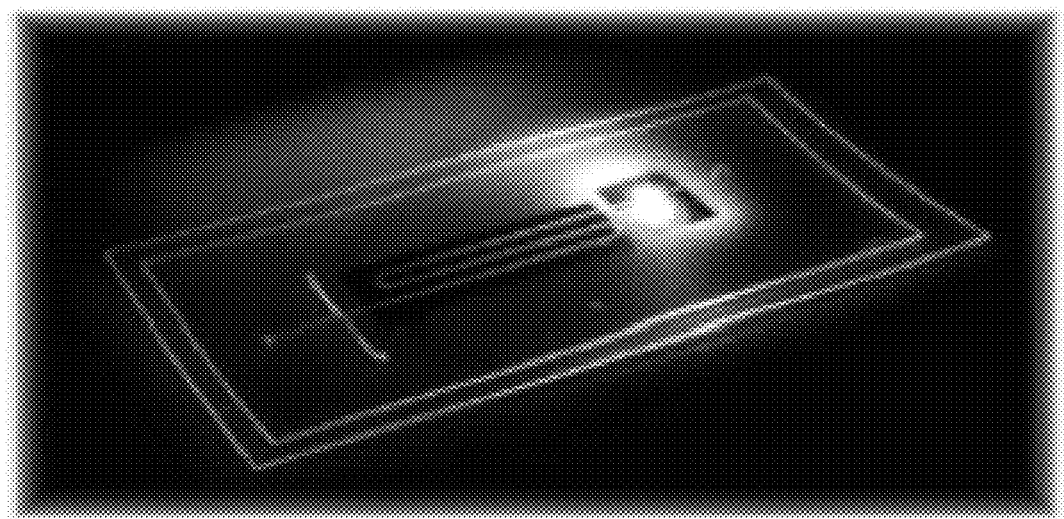
FIG. 9 shows a representative micro-fluidic device with dried active reagent and red blood cell separator.

A micro-fluidic device with dried active reagent and red blood cell separator can be used (FIG. 9). User collects finger-stick whole blood sample with capillary dispenser systems and adds the sample to the sample port. The sample then mixes with a dried active reagent in the device. The sample and the rehydrated reagent then move together through a blood separation chamber. Plasma is analyzed in the read area using a low cost field based spectrometer.

EXAMPLE 6

A Field-deployable, Rapid Cyanide Test

This example describes steps of a representative field-deployable, rapid cyanide test (FIG. 10). Step 1: Adsorb finger-stick blood sample into sponge impregnated with the cobinamide-conjugate. Step 2: Squeeze tube containing lysis reagent to release buffer, and then mix the buffer, blood and cobinamide-conjugate. Step 3: Insert collection tube into test device, and sample will flow through filter to remove cellular debris, etc., through membrane coated with capture reagent (streptavidin). Step 4: Incubate and slide sample tube holder/optical module over capture zone. Step 5 can be any of the following scenarios 5a-5c. Step 5a: Digital readout displays result as "negative" for cyanide. Step 5b: Digital readout displays result as "low positive" for cyanide. Step 5c: Digital readout displays result as "positive" for cyanide.

All headings are for the convenience of the reader and should not be used to limit the meaning of the text that follows the heading, unless so specified.

Citation of the above publications or documents is not intended as an admission that any of the foregoing is pertinent prior art, nor does it constitute any admission as to the contents or date of these publications or documents.

While various embodiments of the invention have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. Thus the breadth and scope of the present disclosure should not be limited by any of the above-described exemplary embodiments.

REFERENCES

1. Baskin and Brewer, In Medical Aspects of Chemical and Biological Warfare, Eds. Sidell, Takafuji and Franz, TMM publications, Washington, 1997, Chapter 10, pages 271-286.

2. Baud et al., 1991, N. Engl. J. Med., 325: 1761-1766.
3. Boehringer et al., 2012, SPIE Proceedings Vol. 8371.
4. Broderick et al., 2005, J Biol. Chem. 280: 8678-8685.
5. Clark et al., 1981, Lancet i: 1332-1335.
6. Ishii et al., 1998, Anal. Chem., 70(22): 4873-4876.
7. Moriva and Hashimoto, 2001, J. For. Sci., 46(6): 1421-1425.
8. Renz, 1971, Methods Enzymol. 18: 82-86.
9. Way, 1984, Annu. Rev. Pharmacol. Toxicol. 24: 451-481.

We claim:

1. A kit for detecting the presence, absence, or amount of cyanide in a sample, comprising:
a cobinamide conjugate, said cobinamide conjugate comprising a carrier and a cobinamide moiety covalently conjugated to the carrier.

2. The kit of claim 1, further comprising a composition for sample collection, or a composition for sample processing, or a composition for capturing the cobinamide conjugate capable of capturing a multiplicity of the cobinamide conjugates, or any combination thereof.

3. A device for detecting the presence, absence, or amount of cyanide in a sample, comprising:
a chamber housing a cobinamide conjugate, said cobinamide conjugate comprising a carrier and a cobinamide moiety covalently conjugated to the carrier,
wherein the absorbance of light by the cobinamide conjugate after contacting a sample indicates the presence, absence, or amount of cyanide in the sample.

4. The device of claim 3, further comprising:
a second chamber for sample collection, wherein the second and first chambers are the same or different; and/or
a third chamber for housing a composition for sample processing.

5. The device of claim 3, further comprising a solid support for immobilizing the cobinamide conjugate.

6. The device of claim 5, wherein the solid support is configured to allow measurement of the absorbance of light by the immobilized cobinamide conjugate.

7. The device of claim 3, wherein the carrier is a molecule or a surface.

8. The device of claim 3, wherein the cobinamide moiety is directly or indirectly conjugated to the carrier.

9. The device of claim 3, wherein the carrier is capable of being covalently or non-covalently immobilized on a solid support.

10. The device of claim 3, wherein the cobinamide conjugate comprises a multiplicity of cobinamide moieties covalently conjugated to the carrier.

11. The device of claim 3, further comprising a light source.

12. The device of claim 3, further comprising a detector configured to detect the absorbance of light by the cobinamide conjugate.

13. The device of claim 12, wherein the detector detects the absorbance of light by measuring transmittance of light through the cobinamide conjugate, or by measuring reflectance of light from the cobinamide conjugate.

14. The device of claim 3, further comprising a display indicating the presence, absence, or amount of cyanide in the sample.

15. The kit of claim 1, further comprising a solid support for immobilizing the cobinamide conjugate.

16. The kit of claim 15, wherein the solid support is configured to allow measurement of the absorbance of light by the immobilized cobinamide conjugate.

17. The kit of claim 15, wherein the solid support comprises plastic, glass, silica, latex, a nitrocellulose membrane, or a nylon membrane.

18. The kit of claim 1, wherein the carrier is a molecule or a surface.

19. The kit of claim 1, wherein the cobinamide moiety is directly or indirectly conjugated to the carrier.

20. The kit of claim 1, wherein the cobinamide conjugate comprises a multiplicity of cobinamide moieties covalently conjugated to the carrier.

* * * * *